(12) United States Patent
Sun et al.

(10) Patent No.: US 9,358,079 B2
(45) Date of Patent: Jun. 7, 2016

(54) BUR AND METHOD OF MAKING SAME (75) Inventors: Steven Shuwen Sun, Ottawa (CA); Allison Olegario, Nepean (CA); Keith Leslie Stewart, Cardinal (CA); Sai Wai Ip, Ottawa (CA)

(73) Assignee: Sybron Canada LP, Morrisburg (CA)

( * ) Notice: Subject to any disclaimer, the term of this patent is extended or adjusted under 35 U.S.C. 154(b) by 1458 days.

(21) Appl. No.: 12/704,064

(22) Filed: Feb. 11, 2010

(65) Prior Publication Data
US 2011/0195377 A1 Aug. 11, 2011

(51) Int. Cl.
*A61C 3/02* (2006.01)
(52) U.S. Cl.
CPC ............. *A61C 3/02* (2013.01); *Y10T 29/49826* (2015.01)
(58) Field of Classification Search
CPC .................................................. Y10T 29/49826
USPC ...................................... 433/165, 166; 29/428
See application file for complete search history.

(56) References Cited

U.S. PATENT DOCUMENTS

| 2,334,755 | A |   | 11/1943 | Eglinton |
|---|---|---|---|---|
| 2,695,452 | A | * | 11/1954 | Christian ...................... 433/165 |
| 2,708,853 | A |   | 5/1955 | MacLean |
| 3,670,416 | A |   | 6/1972 | Kreder |
| 3,971,135 | A |   | 7/1976 | Leu |
| 4,627,665 | A |   | 12/1986 | Ewing et al. |
| 5,098,233 | A |   | 3/1992 | Patterson et al. |
| 5,332,339 | A |   | 7/1994 | Nakayama et al. |
| 5,809,854 | A |   | 9/1998 | Thielen et al. |
| 6,589,671 | B1 |   | 7/2003 | Kehrer |
| 7,021,933 | B2 |   | 4/2006 | Caldwell |
| 7,094,055 | B2 |   | 8/2006 | Senia et al. |
| 7,232,311 | B1 |   | 6/2007 | Greggs |
| 2006/0188843 | A1 |   | 8/2006 | Furney |
| 2009/0170053 | A1 |   | 7/2009 | Ikemi |
| 2009/0224530 | A1 |   | 9/2009 | Sessions |

FOREIGN PATENT DOCUMENTS

| GB | 659359 A | 10/1951 |
|---|---|---|
| GB | 692749 | 6/1953 |
| GB | 842845 A | 7/1960 |

(Continued)

OTHER PUBLICATIONS

International Searching Authority, Search Report and Written Opinion in International Patent Application No. PCT/IB2011/000428, dated Jul. 7, 2011.

(Continued)

*Primary Examiner* — Heidi M Eide
(74) *Attorney, Agent, or Firm* — Wood, Herron & Evans, LLP (57) ABSTRACT

A bur for use with a machine comprises a head and a shank that are made of dissimilar materials with a joint between the head and the shank. The material of the head has a lower coefficient of thermal expansion than the material of the shank. The shank has a recess in one end. The head has a working surface and a projecting portion that cooperates with the recess. The joint is formed at an interface between the projecting portion and the recess whereby a portion of the head that includes the projecting portion is compressively stressed. The projecting portion may have a cone-like shape and the recess may have a cup-like shape. The material of the shank may be stainless steel and the material of the head may comprise metal carbide. The bur may be a dental bur.

19 Claims, 6 Drawing Sheets

(56) References Cited

FOREIGN PATENT DOCUMENTS

| JP | H09-75373 A | 3/1997 |
|----|-------------|--------|
| JP | 2009-056002 A | 3/2009 |
| WO | 2009107595 A1 | 9/2009 |

OTHER PUBLICATIONS

Larry McNally, "Dreams of Precision Manufacturing: Beavers Dental of Morrisburg, Ontario," Scientia Canadensis: Canadian Journal of the History of Science, Technology and Medicine, vol. 19, (48) 1995, p. 76-87.

Chinese Patent Office, Office Action in Chinese Patent Application No. 201180017348.6, dated Nov. 10, 2015.

Chinese Patent Office, Office Action in Chinese Patent Application No. 201180017348.6, dated Mar. 18, 2015.

Chinese Patent Office, English translation of Office Action in Chinese Patent Application No. 201180017348.6 dated Mar. 18, 2015.

* cited by examiner

BUR AND METHOD OF MAKING SAME

TECHNICAL FIELD

The invention relates generally to tool bits and, more particularly, to burs for use in material removal.

BACKGROUND

Material removal may be accomplished in many ways. One common method involves bringing a rotating tool bit into contact with the material that is to be removed. For example, in a dental procedure, a dentist may operate a drill holder or handpiece with a tool bit mounted therein. In this application, the bit is referred to as a dental bur or simply a bur and has a surface designed to remove tooth material in a controllable and ideally painless manner. The handpiece is essentially a specially designed drill or rotary machine. The handpiece may be powered or driven in a variety of ways, for example, by compressed air that passes through an air turbine or by electricity via an electric motor such that a bur that is chucked or otherwise held in the handpiece may rotate at rates that may exceed 400,000 rpm.

While a bur may be of a single piece construction, the bur is often an assembly of multiple parts in order to address manufacturing costs and performance criteria. For example, the bur may be a two-part construction that generally includes a head joined to a shank or shaft. The head is designed to remove the targeted material and has an abrasive surface or cutting edges, like teeth or blades, for this purpose. In operation, when the bur is rotated and the cutting edges of the head are brought into contact with a softer material, the edges cut or remove the material. Again, referring to a dental bur as an example, the dentist may use the bur to remove portions of a tooth, such as tooth enamel, during endodontic therapy by bringing the rotating head in contact with the tooth.

To efficiently remove material at a high rate, the blades must remain sharp and penetrate the surface of the material. In this regard, the head of the bur is often made of a material that is harder than the material being removed. The material of choice is metal carbide, like tungsten carbide, though in some applications, diamond impregnated or electrodeposited diamond cutting edges may be used.

The shank functions to transfer the rotation from the handpiece, to the head as well as space the head a distance from the handpiece. Where the bur is constructed of two separate parts, the shank may be made of a low-cost, machinable, high-strength material, for example, steel.

Figure 1A:
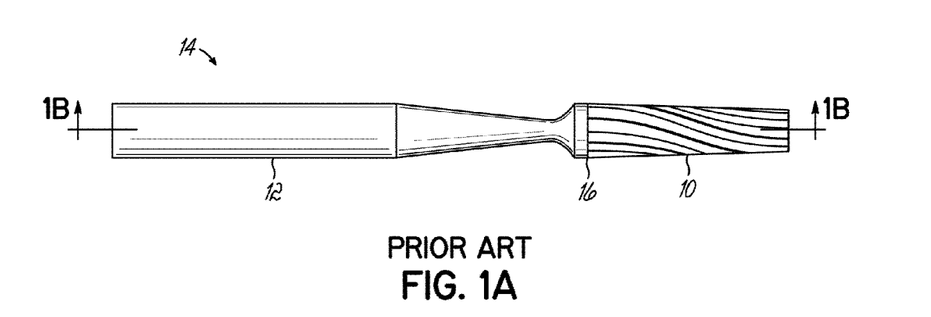
FIG. 1A is a plan view of a bur having a butt joint in accordance with the prior art.
Figure 1B:
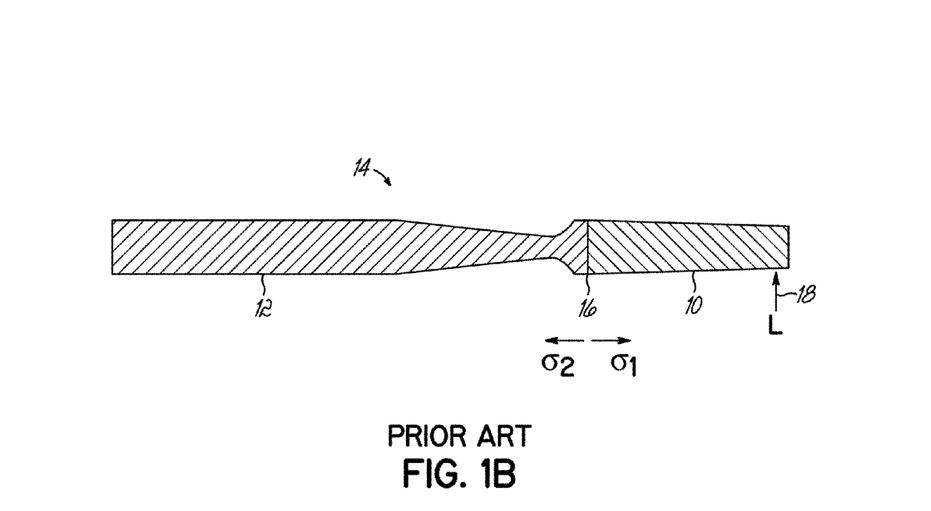
FIG. 1B is a cross-sectional view of FIG. 1A taken along section line 1B-1B.

The carbide piece, prior to joining and machining the cutting edges therein, is often referred to as a pill. With reference to FIGS. 1A and 1B, one technique that is used to join a pill 10 to a shank 12 to make a bur 14 includes forming a butt joint 16 between the two parts. As shown in FIGS. 1A and 1B, the butt joint 16 involves bringing two flat surfaces together, one flat surface on the pill 10 and one on the shank 12, and either welding or brazing the interface between the two flat surfaces to form the butt joint 16. Another joint configuration (not shown) that has been implemented to join the pill and the shank includes forming a recess in the pill and inserting a portion of the shank in the recess and brazing or welding the two together.

However, each of these constructions has its limitations. For one, while the butt joint is a simple, easily formed joint, a bur having a butt joint often breaks under loads encountered during material removal. That is, the joint is often the weak point in this construction, and sometimes limits the useful life and effectiveness of the bur. In particular and with reference to FIG. 1B, a lateral load L (arrow 18) or moment that is placed on the head or pill 10 of the bur 14 during use places surfaces of the bur 14 in tension (represented by $\sigma_1$) and, consequently, the joint 16 is also at least partly in tension. Thus, the stresses caused by the applied load L tend to pull the joint 16 apart. These crack opening stresses (represented by $\sigma_2$) are of the exact same magnitude as the tensile stress $\sigma_1$.

Another joint configuration includes forming a recess in the pill in to which the shank is tilted and joined. However, this joint configuration is costly to machine and often requires specially adapted joining techniques that are generally not practical for manufacturing environments. For example, where the pill is made of tungsten carbide, machining of the recess in the pill usually requires diamond impregnated or other costly drill bits because metal carbides are well known for their extreme hardness. Consequently, machining the recess in a pill made of an extremely hard material adds significant costs to the manufacturing process. Furthermore, this technique may not provide a joint capable of resisting normal stresses encountered during use of the bur.

Consequently, there is a need for a bur that addresses the aforementioned problems. In particular, what is needed is a bur that is both strong and manufacturable in a cost effective manner.

SUMMARY

To these ends, in one embodiment of the invention, a bur for use with a machine having a rotatable chuck comprises an elongated member having a longitudinal axis and includes a head and a shank that are made of dissimilar materials. The head and the shank are joined together at a joint. The material of the head has a lower coefficient of thermal expansion than the material of the shank. The shank includes a gripping portion adapted to cooperate with the rotatable chuck of the machine and a recess formed in one end of, and extending into, the shank in the direction of the longitudinal axis. The head extends along the longitudinal axis and has a working surface adapted to remove material and a projecting portion that cooperates with the recess. The joint is formed at an interface between the projecting portion and the recess whereby a portion of the head that includes the projecting portion is compressively stressed. In one embodiment, the material of the shank is stainless steel and the material of the head comprises metal carbide. In one embodiment, the projecting portion has a cone-like shape and the recess has a cup-like shape that complements the cone-like shape of the projecting portion. In another embodiment, the cone-like shape of the projecting portion has a concave or convex surface and the cup-like shape of the recess has a convex or concave surface, respectively. In one embodiment, the bur is a dental bur.

In another embodiment of the present invention, a method of manufacturing a bur comprises providing a shank that has a longitudinal axis with a recess that extends into the shank along the longitudinal axis from one end thereof, and the shank has a gripping portion adapted for use in a chuck of a machine. The method further comprises providing a pill having a longitudinal axis and a projecting portion that extends along the longitudinal axis of the pill and inserting the projecting portion of the pill into the recess of the shank to form an interface therebetween, whereby the longitudinal axis of the pill and the longitudinal axis of the shank are in substantial alignment. The pill and the shank are joined at the interface to form a joint along at least a portion thereof such that a portion of the pill that includes the projecting portion is compressively stressed. The pill is machined prior to or following joining of the pill to the shank to form a working surface thereon, the working surface being configured to remove material. In one embodiment, joining the pill and the shank includes welding the pill to the shank.

BRIEF DESCRIPTION OF THE DRAWINGS

The accompanying drawings, which are incorporated in and constitute a part of this specification, illustrate embodiments of the invention and, with the general description give above, together with the detailed description given below, serve to explain various aspects of the invention.

DETAILED DESCRIPTION

Referring now to the drawings and to FIGS. 2A and 2B in particular, in one embodiment of the present invention, a bur 100 includes a shank 102 joined to a head 104 at a joint 106, each of which is described in more detail below. As shown, the bur 100 is generally an elongated member 108 having a longitudinal axis 110 around which the bur 100 is designed to be rotated. Also described in more detail below, the shank 102 and the head 104 are made of dissimilar materials such that the materials have different coefficients of thermal expansion. With reference to FIG. 2B, the shank 102 has a recess 112 formed in one end thereof and the head 104 has a complimentary, though opposing, projecting portion 114 such that at least a portion of the projecting portion 114 fits within, mates, or abuts at least a portion of the shank 102 to form the joint 106. While the details of the projecting portion 114 and recess 112 are described more fully below, the configuration of the projecting portion 114 and recess 112 in combination with the difference between the thermal expansion coefficients of the two materials produces compressive stresses in the head 104, particularly in and around the projecting portion 114. The bur 100 is, therefore, unexpectedly strong as the joint 106 between the head 104 and the shank 102 is capable of withstanding greater stresses during use without failure as compared, for example, to the bur 14 having the butt joint 16 configuration as shown in FIG. 1A. Furthermore, while specific reference is made to a "bur" and to dental applications, it will be appreciated that the bur 100 may be suitable for use in other material removal applications, for example, in PC board drilling, and metal cutting and shaping applications. In these applications, the bur may be referred to as a "micro-drill," a "bit," a "cutter," or another similar term, and, thus, the term "bur" does not refer only to a dental bur.

Figure 2A:
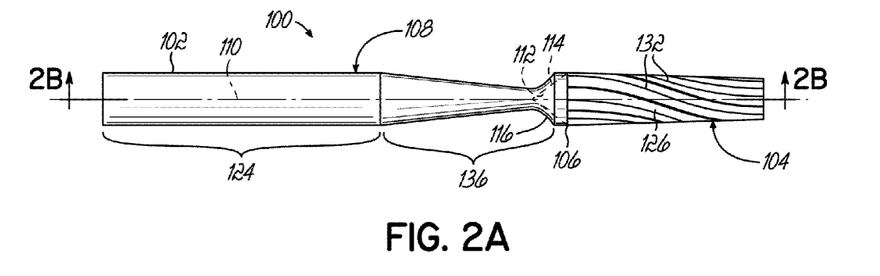
FIG. 2A is a plan view of one embodiment of a bur of the present invention.
Figure 2B:
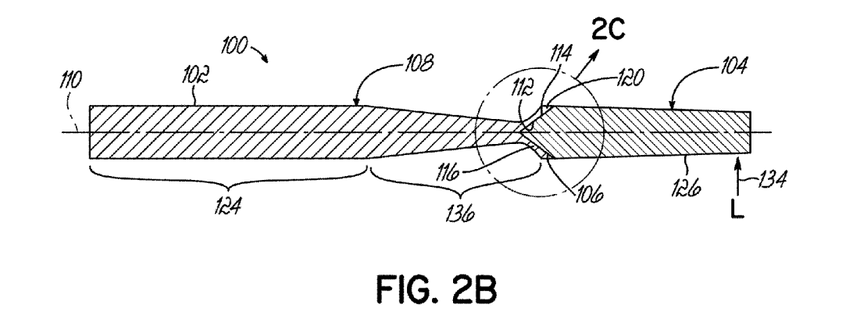
FIG. 2B is a cross-sectional view of FIG. 2A taken along section line 2B-2B.
Figure 2C:
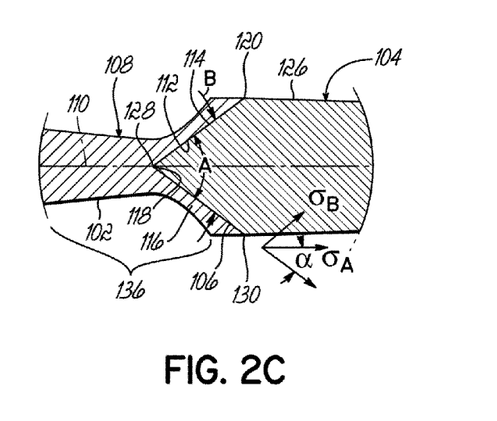
FIG. 2C is an enlarged view of the encircled area 2C of FIG. 2B.

With reference to the shank 102 shown in FIGS. 2A-2C, the recess 112 is formed in one end of the shank 102. As shown, the shank 102 may have a sidewall 116 that defines the recess 112. The recess 112 receives at least a portion of the projecting portion 114 such that the projecting portion 114 cooperates with or abuts a portion of the sidewall 116. In one embodiment, the recess 112 has a generally concave or cup-like shape. In this aspect, the recess 112 may have a multitude of configurations, some of which are described below with reference to FIGS. 3-10. In addition to various cup-like configurations, the surface finish of the sidewall 116 may be rough or be configured with grooves or ridges (not shown) that may be incorporated irrespective of the shape of the recess 112.

Figure 9:
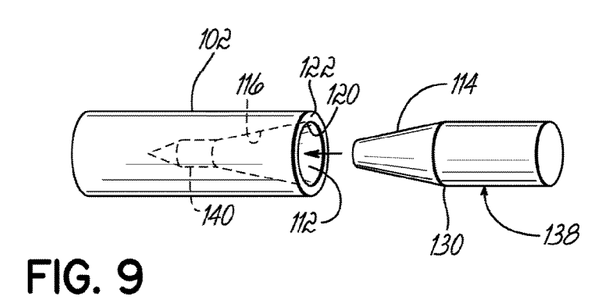

With continued reference to FIGS. 2A-2C, in one embodiment, the recess 112 is a conical shape, and, in particular, may be a cone that is generally symmetrical about the longitudinal axis 110 of the bur 100 and that is defined by an angle A at the vertex 118 of the cone (see FIG. 2C). The angle A may measure, for example, between 0° and 180°. By way of further examples, angle A may measure about 20° or greater, about 30° or greater, or about 40° or greater, and may measure about 160° or less, about 130° or less, about 110° or less, or about 90° or less. By way of additional examples, angle A may measure between about 20° and about 160°, between about 30° and about 90°, between about 40° and about 80°, or between about 55° and about 65°. In one embodiment, angle A is about 60°. The base of the conical recess 112 may be defined by a rim 120 of the sidewall 116. As shown, the rim 120 may coincide with the cross-sectional dimension of the shank 102 at the joint 106; however, embodiments of the present invention are not so limited. For example and as illustrated in FIG. 9, the rim 120 may have a cross-sectional dimension that is less than a cross-sectional dimension of the shank 102 at this location. The difference between the cross-sectional dimension of the rim 120 and the cross-sectional dimension of the outer surface of the shank 102 may form a ledge 122, as shown.

With reference to FIGS. 2A and 2B, as introduced above, the shank 102 is joined to the head 104 and allows the bur 100 to be rotated around its longitudinal axis 110. To that end, the shank 102 may be configured to be secured within a drill (not shown) or similar device that is capable of forcibly rotating the bur 100. By way of example, in dental applications, the drill may be a handpiece. In this regard, the shank 102 has a gripping portion 124 that cooperates with the drill and may be configured specifically for the drill. As shown in FIG. 2A, the gripping portion 124 may be generally spaced apart from the head 104 to provide clearance between the head 104 and the drill to allow a user (for example, a dentist) to see the location of the head 104 during use. To that end, the length of the shank 102, including the gripping portion 124, may vary according to application, including the type of drill as well as the other dimensions of the bur 100. By way of example, the length of the bur 100 may be about 0.700 inches (about 17.8 mm). In addition, while the gripping portion 124 may have any number of configurations that depend on the type of drill and the application, among others, in one embodiment, the gripping portion 124 may have a circular cross section that allows the bur 100 to be frictionally secured within a chuck or tool holder, for instance, a jaw-type or collet-type chuck. By way of example, for circular cross sections, the diameter of the shank 102 may be about 0.063 inches (about 1.60 mm) to about 0.092 inches (about 2.29 mm) though smaller or larger diameters are contemplated. As is known, these and other types of chucks rely on a friction fit to secure the bur 100, particularly those having circular cross sections, in place during use. However, the gripping portion 124 may have other cross-sectional configurations depending on the application and the drill or machine in which the bur 100 is held during use. By way of additional example, the gripping portion 124 may have a square or other non-circular cross-sectional shape such that it may fit within a similarly-shaped tool holder in the rotatable portion of the drill or may otherwise be more firmly gripped by the chuck. In addition or in the alternative, the cross-sectional shape of the gripping portion 124 may have features, such as, projections, a flat, or a key of one type or another, that allow the bur 100 to be secured within and/or driven by the drill.

As set forth above, the shank 102 and the head 104 are made of dissimilar materials and thus have different coefficients of thermal expansion. The difference in thermal expansion between the material of the shank 102 and the material of the head 104 may be used to enhance the strength of the bur 100. With regard to the coefficient of thermal expansion, the material of the shank 102 is characterized by having a thermal expansion coefficient that is higher than that of the head 104, described below. It will be appreciated that the coefficient of thermal expansion of a given material describes the expansion and contraction of the material when the temperature of the material changes. It may be described quantitatively as a ratio of the change of length per unit length, or as a ratio of the change of volume per unit volume, to a change in temperature. It is common to express the coefficient of linear thermal expansion in units of $\mu m/m \cdot K$ or $\mu in/in \cdot °F$. In general, therefore, a material with a relatively large coefficient of thermal expansion will expand more when heated or cooled than a material with a lower coefficient of thermal expansion when each material is subject to the same temperature change. As is known, the coefficient of thermal expansion varies with temperature. Therefore, one of ordinary skill in the art will often refer to an average coefficient of thermal expansion over a particular temperature range.

With reference to FIGS. 2A and 2B, due to the thermal expansion difference, the shank 102 will expand and contract in a greater proportion than the head 104 over the same temperature range. By way of example and not limitation, the shank 102 may be steel, such as carbon steel or austenitic or martensitic stainless steel or other steels that contain chromium as a major alloying element. By way of example, the carbon steel may be an S2 tool steel having an average coefficient of thermal expansion of about 14.8 $\mu m/m \cdot K$ in a temperature range of about 21° C. to about 750° C. However, other tool steels may be used. By way of additional example, the shank 102 may be made of a 400-series stainless steel or equivalent that contains little (e.g. less the 2.5 wt. %), if any, nickel as an alloying element. Furthermore, the steel of the shank 102 may be in an unhardened state or hardened according to processes known in the art. With regard to the average linear coefficient of thermal expansion, stainless steels may be characterized as having average coefficients of linear thermal expansion in the range of about 10 to about 20 $\mu m/m \cdot K$ in a temperature range from 0° C. up to 1000° C. However, it will be appreciated that the average coefficient of linear thermal expansion of a given steel will depend on the type of steel, particularly the amount and kind of any alloying elements in the steel as well as the temperature range over which the coefficient of thermal expansion is measured. Therefore, the average coefficient of thermal expansion of the shank 102 may be higher than 20 $\mu m/m \cdot K$ or lower than 10 $\mu m/m \cdot K$ provided that the average coefficient of thermal expansion is greater than the average coefficient of thermal expansion of the material of the head 104. Further, it will be appreciated that burs that have a shank 102 of a material that has an average coefficient of thermal expansion that is only slightly greater than the average coefficient of thermal expansion of the head 104 may not exhibit a significant magnitude of strength improvements but may still contain compressive stresses in at least the projecting portion 114 of the head 104, as set forth in more detail below.

In addition to a difference in the coefficient of thermal expansion, the material of the shank 102 has other mechanical properties that may differ from the material of the head 104. For instance, the material of the shank 102 may be softer than, that is, not as hard as, the material of the head 104 though the material of the shank 102 generally has a greater toughness than the material of the head 104. Accordingly, this may allow the gripping portion 124 of the shank 102 to be more effectively secured within the drill where, for example, the jaws of a chuck are harder than the shank 102 and allow the jaws to "bite" into the gripping portion 124 of the shank 102 though the shank 102 does not break due to stresses imposed on it during use.

In one embodiment, the shank 102 is made of stainless steel. Thus, advantageously, the stainless steel shank may resist corrosion when exposed to fluids, such as biological fluids, and other corrosive environments during use. Furthermore, unlike prior art burs with carbide heads, a bur having a stainless steel shank joined to a carbide head according to one embodiment of the invention is strong enough to be used in dental applications. This is despite the relatively large difference between the coefficient of thermal expansion of stainless steel and the metal carbide. In addition, where corrosion resistance is desired, use of stainless steel may advantageously eliminate subsequent plating or processes, such as nickel plating, that may be used to place a corrosion resistant coating on the shank 102. The resistance to corrosion may extend the useful life of the bur 100. For example, a bur 100 having a stainless steel shank may last longer than a bur with a carbon steel shank. Even though the heads on each of a stainless steel shank and a carbon steel shank may have an equivalent useful life, a bur having a stainless steel shank may, nevertheless, outlast a bur having a carbon steel shank because the carbon steel may corrode. Corrosion may cause degradation of the strength of the shank 102 and hence reduce the useful life thereof. Moreover, corrosion of the shank 102 may have particular ramifications in dentistry. While the corrosion products may not be a biological hazard and while a corroded shank may retain sufficient strength such that it does not break or deform during use, the discoloration of a bur due to corrosion of the shank is not aesthetically pleasing and will appear "dirty" to patients who may then object to the use of the corroded bur in their mouths.

As shown in FIGS. 2A-2C, the head 104 forms one end of the bur 100 that is generally opposite the gripping portion 124 of the shank 102. As set forth above, the projecting portion 114 cooperates with the recess 112 of the shank 102 to form the joint 106. The head 104 of the bur 100 is designed to remove material when the bur 100 is rotated. To accomplish material removal, the head 104 has a working surface 126. With reference to FIG. 2A, the working surface 126 is configured with projections 132 or other suitable features and is thereby capable of removing material from a work piece (not shown). One of ordinary skill will observe that there are many suitable projections and that selection of the type of projection often depends on the application for which the bur 100 is designed. In dentistry, for example, the working surface 126 may be designed to remove tooth enamel. By way of example only, and not limitation, the projections 132 may be a plurality of blades spaced apart by flutes (by way of example, shown in FIG. 11B) that are machined into the head 104. These blades may be positioned at different angles relative to a tangent to the working surface 126 in order to change the cutting action of the bur 100. As is known, more obtuse angles will produce a so-called "negative rake angle" which increases the strength and longevity of the bur 100. On the other hand, more acute angles will produce a "positive rake angle" such that the blades are "sharper." However, blades having positive rake angle may dull more quickly. The blades may have additional features. By way of example and with specific reference to FIG. 11B, additional cuts across each blade may be added to increase cutting efficiency.

With reference to FIG. 2A, the working surface 126 may take a cylinder-like shape, however, embodiments of the present invention are not so limited. The shape of the head 104, other than the projecting portion 114, may depend on a given application, machine, or material and may include spherical, inverted cone, straight fissure, tapered fissure, and pear-shaped heads, among others. Furthermore, the cross-sections of the head 104, joint 106, and shank 102 need not be similar in dimension or in shape. For instance, the cross-sectional dimension of the head 104 may be greater than, equal to, or less than the cross-sectional dimension of the shank 102.

With regard to the projecting portion 114, the surface of the projecting portion 114 opposes the sidewall 116 of the shank 102 at the joint 106. To that end, the projecting portion 114 is configured to at least partially fit within the recess 112 such that a portion of the surface of the projecting portion 114 abuts the surface of the sidewall 116. The projecting portion 114 may, therefore, be concave relative to the butt joint 16 (shown in FIGS. 1A and 1B). The concave shape of the projecting portion 114 may take any one of a number of configurations, some of which are described below with reference to FIGS. 3-10.

In one exemplary embodiment, as is shown in FIGS. 2A-2C, the projecting portion 114 may correspond to the dimensions of the recess 112 such that nearly the entire surface of the sidewall 116 abuts the entire surface of projecting portion 114. Therefore, where the recess 112 has a conical shape, the projecting portion 114 may also be a similar conical or cone shape. As shown, the cone-shaped projecting portion 114 may be generally symmetrical and be defined by an angle B at the vertex 128 or tip of the cone, and the base of the cone may correspond in cross-sectional dimension to the intersection of the working surface 126 with the surface of the projecting portion 114 at a shoulder 130. In one embodiment, angle B may substantially correspond to angle A of the recess 112, although it will be appreciated that the two angles may differ to, for example, simplify assembly, as set forth in detail below.

As with the recess 112 described above, in one embodiment, the vertex 128 of the projecting portion 114 may reside on the longitudinal axis 110 and may measure, for example, between 0° and 180°. By way of further examples, angle B may measure about 20° or greater, about 30° or greater, or about 40° or greater, and may measure about 160° or less, about 130° or less, about 110° or less, or about 90° or less. By way of additional examples, angle B may measure between about 20° and about 160°, between about 30° and about 90°, between about 40° and about 80°, or between about 55° and about 65°. In one embodiment, angle B is about 60°. As compared to the cross-sectional dimensions of the shank 102 at the joint 106, the cross-sectional dimension of the base of the projecting portion 114, for example, at the shoulder 130, may be larger than, substantially the same dimension as, or smaller than the cross-sectional dimension of the rim 120. Therefore, the projecting portion 114 may or may not completely seat within the recess 112. However, in the exemplary embodiment shown, the dimensions of the shoulder 130 coincide with the rim 120 at the joint 106.

As introduced above, the material of the head 104 has a lower coefficient of thermal expansion than the material of the shank 102. The material of the head 104 therefore expands less than the material of the shank 102, as described above. For instance, the material of the head 104 may have a coefficient of thermal expansion that is lower than about 20 µm/m·K or lower than about 10 µm/m·K. By way of example, the material of the head 104 may have an average coefficient of thermal expansion that is at least about 30% less than the average coefficient of thermal expansion of the material of the shank 102. In a further example, the material of the head 104 may have an average coefficient of thermal expansion that is at least about 50% less than the average coefficient of thermal expansion of the material of the shank 102, and in some cases, the material of the head 104 may have an average coefficient of thermal expansion up to about 70% less than the average coefficient of thermal expansion of the material of the shank 102.

In one embodiment, the material of the head 104 includes metal carbide, for example, a metal carbide of any one or a combination of metals selected from vanadium (V), tungsten (W), chromium (Cr), and/or molybdenum (Mo). However, other types or grades of carbides and other suitable materials having similar hardness and coefficient of thermal expansion may be used. For instance, the head 104 may be a metal oxide; a metal nitride, such as titanium nitride (TiN); or a cermet containing a metal oxide, a metal nitride or another hard ceramic material. Metal carbides, such as tungsten carbide (WC), may have a coefficient of thermal expansion of about 6 µm/m·K. However, the material of the head 104 may be a metal matrix composite that includes any one or a combination of particles of the metal carbide bound in a metal matrix of an alloy of cobalt (Co) and nickel (Ni) or similar metals. By way of example, the metal matrix may contain about 10 wt. % Co. The metal matrix may have an average coefficient of thermal expansion that is greater than the metal carbide. Therefore, the material of the head 104 may have an average coefficient of thermal expansion that is greater than that of the metal carbide alone but that is less than the average coefficient of thermal expansion of the material of the shank 102, as set forth above. It will be appreciated that in the case of metal matrix composites, the coefficient of thermal expansion of the head 104 is determined by the type and proportion of the metal carbide and the type and proportion of the metal matrix. According to the embodiments of the invention, the benefit of a chosen material of the head is not sacrificed to satisfy the minimum strength requirements.

In addition to the difference between the coefficients of thermal expansion of the head 104 and the shank 102, the material of the head 104 is generally harder and more rigid than the material of the shank 102. As is known in the art, metal carbides and other similar materials are generally characterized by hardness in excess of about 8.0 on the Mohs scale, though some are characterized by hardness in excess of about 8.5 and yet others have a hardness of about 9.0 on the Mohs scale. The hardness of the head 104 and the projections 132, in particular, allow the projections to remove materials that are softer, like tooth enamel or a metal. High hardness may improve the material removal while also improving the longevity of the bur 100 in some applications.

In addition, in one embodiment, the material of the head 104 is more rigid than the material of the shank 102. For example, tungsten carbide may be about three times more rigid than steel. However, high rigidity is often associated with brittle materials, that is, materials that break by brittle fracture. As a consequence of the high hardness, as well as other characteristics, the shank 102 may not be made of these materials because the rigidity and hardness of these materials make the shank 102 difficult to grip while also increasing the likelihood that the shank 102 will fail by fracturing during use. However, the shank 102 may be characterized by a hardness that is achievable from being subject to known hardening processes that are associated with the steel from which the shank 102 is made.

Generally, the bur 100 is configured to remove material by contacting a work piece with the bur 100 in a lateral direction, similar to the direction of the load L (arrow 134). By way of contrast, a drill bit removes material by loading the drill bit in an axial direction or 90° from the orientation of the arrow 134. As is known in the art, the load L, when applied in the direction shown in FIG. 2B, will cause a bending moment or torque on the joint 106. Lateral loading thus causes tensile stresses in the bur 100 that are generally parallel to the longitudinal axis 110. Accordingly, a maximum tensile stress $\sigma_A$ may form on the surface of the bur 100 at the joint 106 that is subject to the load L. Tensile stress $\sigma_A$ causes a crack opening stress $\sigma_B$ to form substantially perpendicular to the interface of the joint 106. The crack opening stress $\sigma_B$ is a tensile stress that is oriented substantially perpendicular to the interface in the joint 106 and operates to pull the joint 106 apart. It will be appreciated that the crack opening stress $\sigma_B$ will cause the bur 100 to break when that stress exceeds the tensile strength of the joint 106.

According to one embodiment of the present invention, the recess 112 and the projecting portion 114 are configured to reduce the crack opening stress $\sigma_B$ observed at the joint 106. To that end, in one embodiment, at least a portion of the joint 106 is oriented at an angle a relative to the tensile stress $\sigma_A$. In other words, the joint 106 is not parallel to the applied load such that the tensile stress $\sigma_A$ is not perpendicular to at least a portion of the joint 106. Therefore, along the portion of the joint 106 that is oriented at the angle α, the crack opening stress $\sigma_B$ is reduced from being of about the same magnitude as the tensile stress $\sigma_A$ to a value that is less than $\sigma_A$. In general, as the angle α decreases from 90° (i.e., away from an orientation where a portion of the joint 106 is parallel to the applied load L), the crack opening stress $\sigma_B$ decreases.

The configuration of the joint 106, that is, the interface of the projecting portion 114 with the recess 112, generally determines the angle a in any given cross section of the bur 100. By way of example, and with continued reference to FIG. 2C, in the case of a conical projecting portion 114 that abuts the sidewall 116 that defines the recess 112, the angles A and B generally determine the angle α. As the angles A and B decrease, angle α decreases and the crack opening stress $\sigma_B$ is reduced relative to the tensile stress $\sigma_A$ observed due to loading. In one embodiment, the crack opening stress $\sigma_B$ is at least about 30% less than the crack opening stress observed in a comparative tool having a butt joint. In one embodiment, the crack opening stress $\sigma_B$ is up to about 50% less than the crack opening stress observed in a comparative tool having a butt joint. As a specific example, where the angles A and B of the recess 112 and the projecting portion 114 at the respective vertices 118, 128 are each about 60°, angle α is about 30°. Further, in this embodiment, the angle α is substantially constant along the interface between the longitudinal axis 110 of the bur 100 and the outer surface of the joint 106. However, with reference to FIG. 2C, it will be appreciated that embodiments of the present invention are not so limited as the angle a may vary at any point between the longitudinal axis 110 and the outer surface of the joint 106 depending on the configuration of the recess 112 and the projecting portion 114. This may have additional advantages, as is described more fully below.

Figure 6:
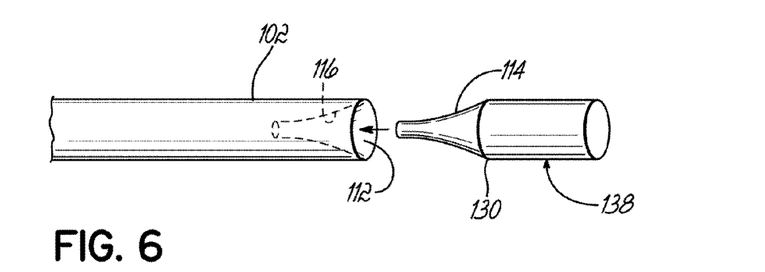
Figure 7:
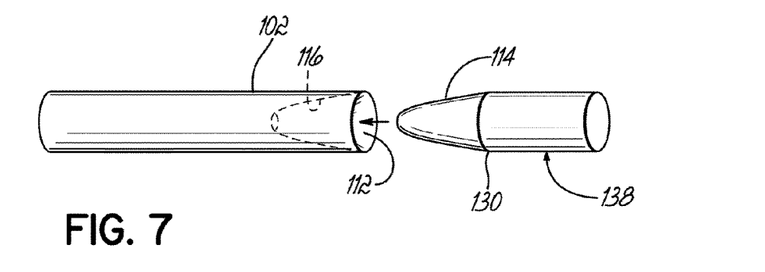

In addition and in accordance with another embodiment of the present invention, the strength of the joint 106 may be increased by increasing the surface area of the interface between the head 104 and the shank 102 at the joint 106 for a given cross-sectional dimension. Generally, as the surface area at the interface increases, the crack opening stress $\sigma_B$ decreases because the tensile stress $\sigma_A$ imposed by the load L is spread over a greater area. The increase in the surface area is due to the configuration of the joint 106. It will be appreciated that there are a number of ways to increase the surface area between the shank 102 and the head 104 without increasing the cross-sectional dimensions of the joint 106. By way of example, increasing the convex/concave nature (i.e., making the projecting portion 114 more convex and the recess 112 more concave as shown in FIGS. 6 and 7, for example) of the joint 106 may increase the area of the interface. This may be accomplished by variation of the angle a between the longitudinal axis 110 and the outer surface of the joint 106 at points along the interface of the joint 106. That is, the interface between the sidewall 116 and the projecting portion 114 along one or more cross sections of the bur 100 may be curvilinear. It will be appreciated that as the interface becomes progressively more curved, the surface area of the interface will generally increase. Alternatively or in conjunction with the above, decreasing the angles A and B at the vertices 118, 128 of the recess 112 and the conical projecting portion 114 will also increase the surface area in the joint 106.

As introduced above, at least a portion of the projecting portion 114 is compressively stressed when the bur 100 is not in use. That is, at least a portion of the projecting portion 114 contains residual compressive stresses. Residual compressive stress act to reinforce the bur 100 and thereby strengthen the bur 100 against failure. The compressive stresses result from the configuration of the projecting portion 114 and the sidewall 116 together with the difference in thermal expansion between the material of the head 104 and the material of the shank 102, each described above.

In one embodiment, residual compressive stresses are formed in at least the projecting portion 114 once the head 104 and the shank 102 are joined together, as described below. This stands in contrast to a butt joint shown in FIGS. 1A and 1B where it was discovered that the configuration of the joint 106 results in tensile stresses in the head 104 near the joint 106. Furthermore, as the difference between the coefficients of thermal expansion increase, the strength of the butt joint may decrease and/or the residual tensile stresses may increase. It will be appreciated that metal carbide, while being hard, is also more brittle than steel, and when objects made therefrom are subject to tensile stress, they may fracture. In other words, the materials of the head are weak in tension. Consequently, residual tensile stresses act to weaken the bur, particularly in regions of the head, which may cause the head to "pop off" following butt joining.

Advantageously, according to embodiments of the invention, at least a portion of the projecting portion 114, and in some embodiments, a portion of the working surface 126 of the head 104, contains residual compressive stresses. For the compressed surface to be subject to tensile stress sufficient to cause the bur 100 to break, the applied load must first be of sufficient magnitude to overcome the residual compressive stress before any tensile stress is observed. Thus, the residual compressive stress in the head 104 results in a net increase in the strength of the bur 100. In sum, as a result of the configuration of the projecting portion 114 and the configuration of the recess 112, which reduce the crack opening stress $\sigma_B$ observed at the joint 106, and the residual compressive stresses in at least a portion of the head 104, which increases the strength of at least the joint 106, the burs of the present invention withstand greater loading without breakage as compared to similar burs having butt joints.

In another embodiment of the invention and with reference to the FIGS. 2A-2C, the bur 100 has a neck portion or neck 136 between the gripping portion 124 and the joint 106. As shown, the neck 136 is a region along the longitudinal axis 110 of the bur 100 of reduced cross-sectional dimension. The neck 136 may have the smallest cross-sectional dimension of the bur 100. In one embodiment, the cross-sectional dimension of the neck 136 is less than a maximum cross-sectional dimension of the joint 106. By way of example, the neck 136 may measure between about 0.018 inches (about 0.046 mm) to about 0.020 inches (about 0.05 mm). In the embodiment shown, the neck 136 is configured as a taper from the gripping portion 124 to a minimum cross-sectional dimension near but not at the joint 106 where the neck 136 then tapers to the cross-sectional dimension of the joint 106. The neck 136 may therefore provide a reference distance that allows the user to gage the depth or location of the head 104 relative to the work piece. For example, a dentist may be able to gage the depth that the head 104 is in a tooth by observing the proportion of the neck 136 that is visible.

Figure 3:
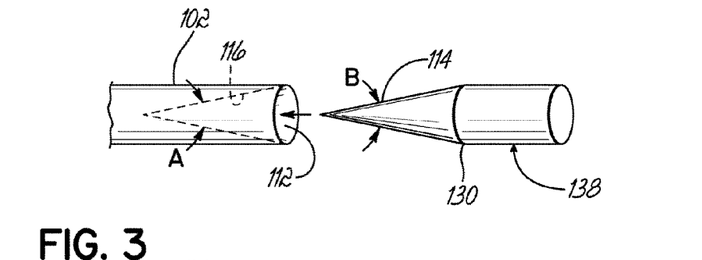
FIGS. 3-10 are perspective exploded views of embodiments of the pill and shank configuration according to the invention.
Figure 10:
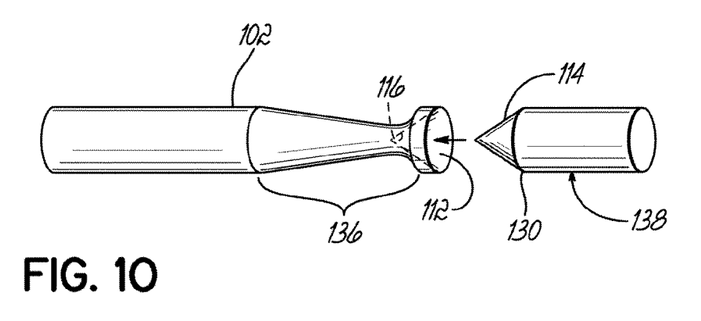
Figure 11A:
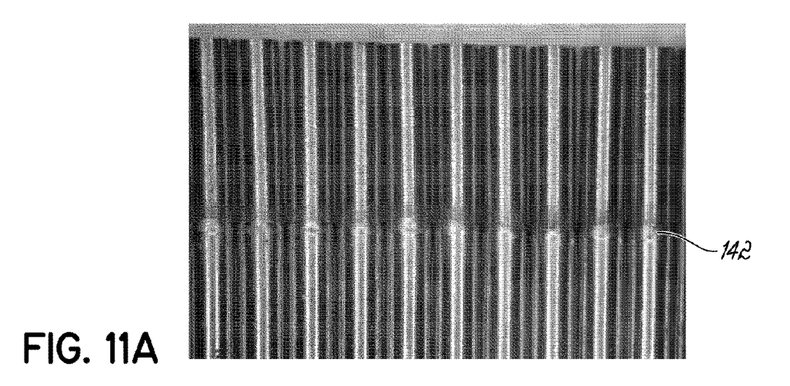
FIG. 11A is a photograph of a plurality of blanks of one embodiment of the present invention.
Figure 11B:
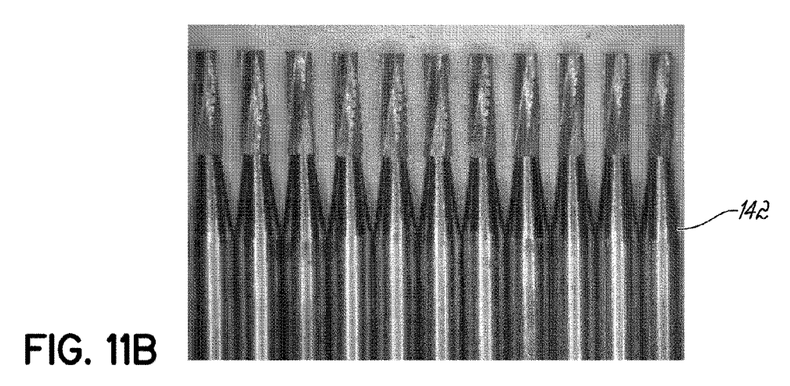
FIG. 11B is a photograph of a plurality of burs according to one embodiment of the present invention following machining of the blanks of FIG. 11A.

With reference to FIG. 3, embodiments of the bur 100 described above are made by joining the shank 102 of one material having a recess 112 in an end thereof to a pill 138 of another material having a projecting portion 114 at an end thereof to form a blank (depicted in the photograph of FIG. 11A), and then machining the other end of the pill 138 to form the head 104 (e.g., as shown in FIG. 2A), and, optionally, machining the shank 102 to form the gripping portion 124 and the neck 136 (e.g., as shown in FIG. 10) to form a bur (depicted in the photograph of FIG. 11B). However, it will be appreciated that machining the neck 136 and/or gripping portion 124 may occur before joining the shank 102 with the pill 138. To that end, the shank 102 may be cut from a commercially available bar stock and may be machined to the desired cross-sectional dimensions according to methods known in the art. Machining may include machining the recess 112 in one end of the bar stock and/or machining the gripping portion 124 at the other end thereof and/or the neck 136 therebetween to form the shank 102. However, the shank 102 may be prepared according to other methods known in the art, such as by casting, powdered metallurgy, or forging process, where the shank 102, including the recess 112 and, optionally, the gripping portion 124 and/or the neck 136, may be formed with or without finish machining. In particular, the recess 112 may have any one of a variety of configurations in accordance with the principles described above. The cup-like configuration of the recess 112 may be formed with a lathe or other similar metal-cutting equipment such that the sidewall 116 of the shank 102 defines a cone (as shown), for example, or other symmetrical cup-like recess. However, it will be appreciated that the recess 112 need not be symmetrical though one of ordinary skill in the art will appreciate that a symmetrical recess may be more easily machined with a lathe or similar equipment.

Figure 4:
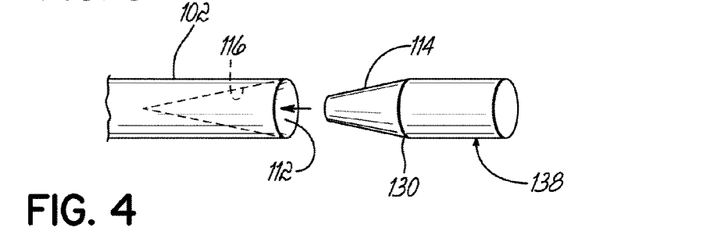
Figure 5:
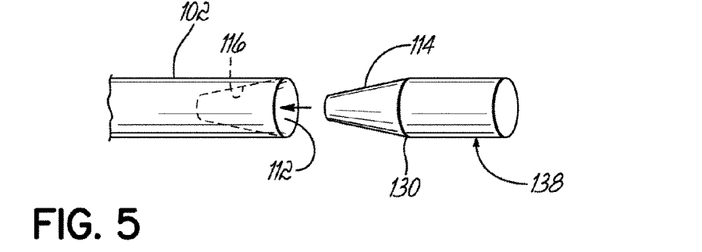

With reference to the exemplary embodiments shown FIGS. 3-10, the recess 112 may have a cone-like or conical configuration. For instance, the recess 112 may be in the shape of the cone, as shown in FIGS. 3 and 4. However, the recess 112 may have other concentric cone-like shapes, such as a truncated cone as shown in FIG. 5. Other modified cup-like shapes may include convex and concave cone-like shapes, as shown in FIGS. 6 and 7, respectively. In these embodiments, the joint 106 would be curvilinear over a cross section through the joint.

Figure 8:
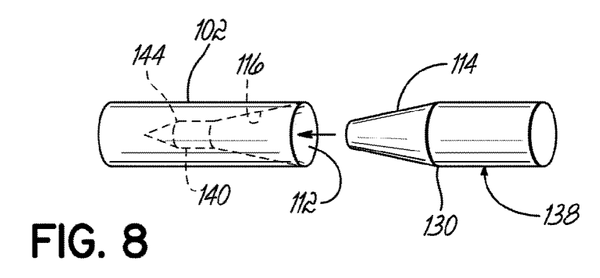

With reference to FIGS. 8 and 9, still other modified cup-like shapes include recesses 112 that are formed by first drilling a hole in one end of the shank 102. The hole may help guide subsequent machining of the remaining portion of the recess 112 thereby improving the concentricity of the recess 112 with the outer surface of the shank 102. By way of example, the sidewall 116 of the shank 102 may then appear to have a residual portion of the guide hole 140, as shown. The residual portion of the guide hole 140 may provide relief when the surface of the sidewall 116 abuts the projecting portion 114.

With reference again to the exemplary embodiment shown FIG. 3, the projecting portion 114 of the pill 138 may have a cone-like or conical configuration that cooperates with the recess 112. As set forth above with respect to the head 104, the pill 138 is made of a material that has a coefficient of thermal expansion that is less than the material of the shank 102 and may be harder than the material of the shank 102. The projecting portion 114 of the pill 138 is formed prior to assembly with the shank 102 by machining, casting and/or powder metal processing. For example, the projecting portion 114 of the pill 138 may be machined from a rod of material by grinding the rod with a diamond tool or another sufficiently hard tool. Alternatively, the pill 138 may be formed by a powdered metal process, particularly where the head 104 is a metal matrix composite as is known in the art. For instance, the pill 138 may be made by pressing and sintering a powdered metal compact that includes particles of metal carbide and particles of a metal matrix. In this regard, the projecting portion 114 of the pill 138 may be nearly net shaped and, thus, require little, if any, machining prior to joining with the shank 102. The working surface 126 may be formed in the pill 138 before or after joining with the shank 102. Following the formation of the projecting portion 114, assembly and further machining, if any, the pill 138 becomes the head 104 of the bur 100.

In one embodiment of the invention, the projecting portion 114 of the pill 138 may have a shape that matches the shape of the recess 112. For example, the projecting portion 114 may have a convex shape, such as a cone shape that is shown in FIG. 3. As set forth above, a cone projecting portion 114 may be defined by the vertex 128 with the angle B of the cone measured at the vertex 128. Accordingly, where the shapes of the projecting portion 114 and the recess 112 match, the angle A at the vertex 118 of the recess 112 may measure nearly the same as angle B. However, it will be appreciated that the angle B of the projecting portion 114 or the angle A of the recess 112, or both angles A and B, may be varied to ease assembly of the pill 138 with the shank 102. For example, the angle B of the projecting portion 114 may be less than angle A of the recess 112 to facilitate centering of the pill 138 within the recess 112. This configuration may also provide a small gap between the sidewall 116 and the projecting portion 114 near the vertices 118, 128 of the projecting portion 114 and recess 112, respectively, when the projecting portion 114 abuts the sidewall 116. Accordingly, the relative shapes of the projecting portion 114 and the recess 112 may be configured to align the individual longitudinal axis of each of the pill 138 and the shank 102 with the longitudinal axis 110 of the bur 100 when the shank 102 and pill 138 are brought together.

While the projecting portion 114 and the recess 112 may be substantially the same shape such that the entire surface of each abuts the other, as shown in FIGS. 2, 3, and 5, the invention is not so limited. In other embodiments as shown in FIGS. 4, 8, and 9, the projecting portion 114 may be a truncated cone shape. The truncated cone shape may be machined or formed by sintering a compact to form a cone, as described above, followed by machining to remove the vertex of the cone, or the truncated cone may be formed directly by sintering a compact with little or no post-sintering machining. The corresponding recess may have a cone-like shape, such as that shown in FIGS. 3 and 4. In these embodiments, surfaces of each of the projecting portion 114 and sidewall 116 are not in complete contact with one another. Therefore, when one projecting portion 114 is inserted into the cone-shaped recess 112, a gap or void 144 may be formed in the bur 100.

Following preparation of the shank 102 and pill 138, the shank 102 and pill 138 are assembled by inserting at least a portion of the projecting portion 114 of the pill 138 into the recess 112 of the shank 102. Once assembled, a portion of the projecting portion 114 abuts a portion of the sidewall 116. Where the shapes of the projecting portion 114 and recess 112 differ, the void 144 may be created anywhere in between the projecting portion 114 and the sidewall 116. In one embodiment, the void 144 may be formed near the longitudinal axis 110 of the bur 100 to facilitate the joining process, described below.

Once assembled, the shank 102 and pill 138 are joined or fused together by heating at least the projecting portion 114 and the sidewall 116, and adjacent regions of the shank 102 and head 104, to form a metallurgical bond between the two parts. By way of example, the shank 102 and the pill 138 may be joined by welding or brazing the two parts together. In particular, by way of further example, welding may be achieved by resistance welding, induction welding, or laser beam welding. In welding, the two parts that are to be joined may be pressed together and heated. A layer of molten metal is formed between the two parts that may include material from both. During joining, the interface between the shank 102 and the head 104 may experience temperatures on the order of 1,000° C. or more depending on the materials of the pill 138 and the shank 102. Areas adjacent to the interface are also heated, though these areas do not melt. Additionally, joining may include providing a protective atmosphere around the region where the joint forms. The protective atmosphere may include flowing an inert gas, such as argon (Ar), nitrogen ($N_2$), or helium (He), around the two parts as each is heated and as a layer of molten metal is formed. Once the parts are cooled, the joint 106 is formed. In one embodiment, the weld is formed around the circumference of the rim 120 and may extend along the joint 106 towards the apex 128 to a limited length. Thus, the weld joint 106 may not be formed throughout the interface between the abutting surfaces.

Alternatively, the shank 102 and the pill 138 may be joined by brazing the pill 138 and the shank 102 together. As is known in the art, brazing the shank 102 to the pill 138 may include inserting a filler metal or alloy between the projecting portion 114 and sidewall 116 and heating the sidewall 116 and projecting portion 114 to a melting temperature of the brazing material. Typically this involves heating the shank 102 and the projecting portion 114 to temperatures above 450° C. but lower than the melting temperature of either the material of the shank 102 or the material of the pill 138. Alternatively, brazing may include distributing the brazing material between the pill 138 and the shank 102 where the two parts are close-fitting such that the brazing material enters the interface due to capillary action. In any event, the filler metal is brought above its melting (liquidus) temperature between the two parts. Once the filler metal melts and is then cooled between the pill 138 and the shank 102, a metallurgical bond forms between the brazing material and the shank 102 and between the brazing material and the pill 138 or otherwise joins the two components together. However, due to the added cost of brazing, because of the needed filler material, welding the shank 102 and the pill 138 together is preferred to brazing.

In view of the thermal expansion mismatch between the pill 138 and the shank 102, the heated portions of the shank 102 expand more than the heated portions of the pill 138. Specifically, the diameter of the rim 120 of the recess 112 will expand more than the diameter of the projecting portion 114 at the abutting location. Other areas of the shank 102 that are heated during the joining process also expand to a greater degree than the abutting portions of the projecting portion 114 resulting in an overall enlargement of the recess 112 relative to the abutting portion of the projecting portion 114. The two parts are joined in their respective hot or expanded dimensions. In particular and in one embodiment of the invention, the thermal expansion mismatch between the recess 112 and the projecting portion 114 creates a dimensional mismatch in the region containing the joint 106 at elevated temperatures (due to welding or brazing, as set forth above) relative to the dimensions at room temperature.

Once the shank 102 and pill 138 are joined and then cooled, at least a portion of the dimensional mismatch created at elevated temperature is retained at room temperature. Specifically, during cooling, the heated portions of the shank 102 and head 104 attempt to contract according to their respective coefficients of thermal expansion in an attempt to regain their original, room-temperature dimensions. Due to its higher coefficient of thermal expansion, the shank 102 attempts to contract to a greater extent than the pill 138 but a portion of the shank 102 is constrained from full contraction by its attachment to the head 104. That is, a portion of the shank 102 cannot contract to its original room temperature dimensions. The constrained contraction of the shank 102 produces residual compressive stresses in a portion of the head 104 with a portion of the shank 102 being placed in residual tension. Therefore, at room temperature, at least a portion of the head 104 is in a state of compression with a portion of the shank 102 being in a state of tension. As set forth above, this residual stress state enhances rather than degrades the strength of the bur 100 because the head 104, which is the most susceptible to brittle fracture, is in a state of residual compression that must be overcome during use before any tensile stresses form in these locations.

In one embodiment, the shank 102 and the pill 138 may be pressed together during the joining process. When heated, particularly to temperatures required to weld the shank 102 and pill 138 together, the projecting portion 114 and/or the shank 102 may plastically deform while being held together. Consequently, the exact configuration of projecting portion 114 and sidewall 116 may change upon joining. For example, slight deformation of the shank 102 may occur. This deformation may depend on the temperature to which the shank 102 and pill 138 are heated as well as on the magnitude of the forces, if any, that are used to hold the pill 138 and the shank 102 together while each is heated.

In addition, if not completed prior to joining, the pill 138 may be further machined to form any projections or other surface features of the working surface 126 that are designed to remove material from a work piece. By way of example, post-joining machining may include cutting or machining multiple flutes in the pill 138 to form the head 104. Machining may also include machining away the exterior surfaces of the joint 106. In addition, as is known in the art, burs may be rotated at hundreds of thousands of revolutions per minute such that small misalignments of the pill 138 and the shank 102 during joining may cause the bur 100 to be unbalance or otherwise rotate around an axis that does not coincide with the longitudinal axis 110 of the bur 100. In this case, once the shank 102 and the pill 138 are assembled, additional machining may be required to balance the bur 100 for use at high rotation rates. Although alignment of the individual longitudinal axes is desirable, alignment may not be necessary, particularly where the bur 100 is to be used in applications where the rotation rate is relatively low, or where post-joining machining is to be done.

In order to facilitate a more complete understanding of the invention, the following non-limiting examples are provided.

EXAMPLES

Figure 12:
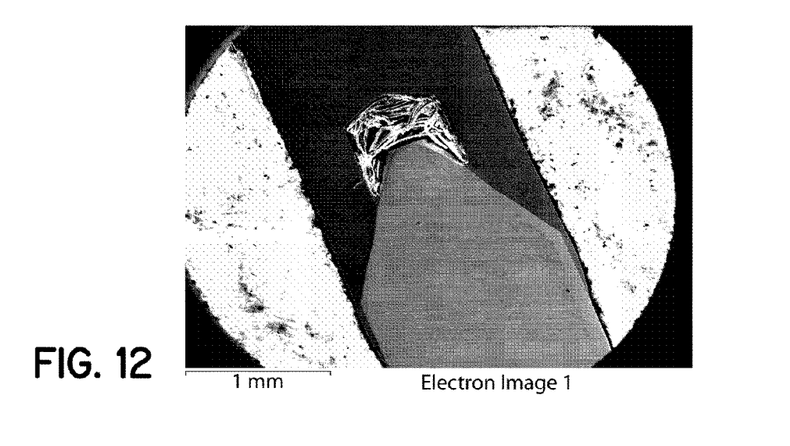
FIG. 12 is a scanning electron micrograph of a cross-section of one embodiment of the present invention.

With reference to FIGS. 11A, 11B, and 12, burs according to one embodiment of the invention were made. The bur shape was No. 557. Cemented tungsten carbide pills with about 6% cobalt (Co) were welded to type 420 stainless steel shanks. The shank and pill were pressed together with a maximum of about 4 pound-force (lbf) and heated in a protective atmosphere until a weld pool formed around the interface. The blanks formed were cooled for about 0.5 seconds in the protective atmosphere and then allowed to air cool to room temperature followed by a post-welding tempering treatment. The blanks are shown in FIG. 11A, prior to machining, and the weld joint is indicated by the arrow 142. The pills were then each machined to form the projections and flutes in each of the heads and the pills were also each machined to form a neck therein, as shown in FIG. 11B.

A cross section taken along the longitudinal axis of one of the blanks of FIG. 11A is shown in FIG. 12. As shown, the projecting portion of the pill has a truncated cone shape (see, e.g., FIG. 8), though an angle at a vertex of a corresponding fully-formed cone would have been about 60°. The recess was also cone-shaped with a residual guide hole made by predrilling the shank prior to cutting the conical taper of the recess (see, e.g., FIG. 8). As shown in FIG. 12, the material in the guide hole is residual steel from the preparation of the sample for microscopic examination. As shown, a solidified weld pool formed around the rim of the pill following welding. However, after welding the outer surface of the joint was removed.

The burs with the joint configuration shown in FIG. 12 were tested to determine the strength as compared to burs with butt joint configurations. To test the burs, the tangent rupture strength of each was measured. Accordingly, a load was applied to the head. The load was gradually increased until the bur broke. The load at failure was recorded. The load at failure for 50 burs is plotted in FIG. 13.

Figure 13:
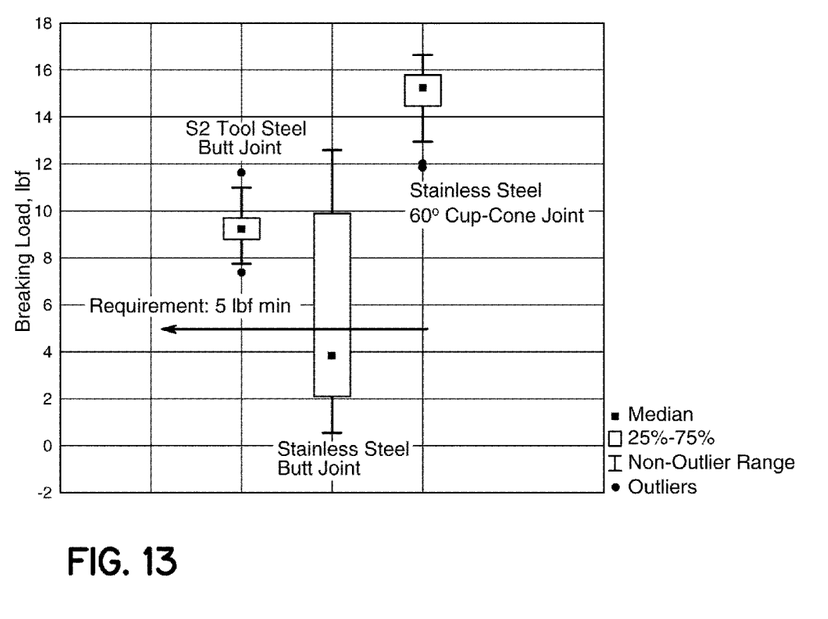
FIG. 13 is a joint configuration-breaking load box plot depicting the load at failure for burs having butt joints and exemplary burs according to one embodiment of the present invention.

FIG. 13 depicts the load at failure of the exemplary burs (labeled "Stainless Steel 60° Cup-Cone Joint") set forth above. FIG. 13 also depicts the load at failure for burs having tungsten carbide heads butt jointed by welding to stainless steel shanks (labeled "Stainless Steel Butt Joint") and the load at failure for burs having tungsten carbide heads butt jointed by welding to an S2 tool steel shank (labeled "Tool Steel Butt Joint").

As shown, the exemplary burs of the present invention are characterized by a load at failure of about 12 lbf (about 53 Newtons) and greater, which exceeds both of the other configurations tested. Furthermore, it was also noted that some of the failures were not located in the joints themselves. Rather, some of the failures occurred in the head or in the neck. Therefore, some of the failure loads of the exemplary burs, as indicated in FIG. 13, are not indicative of the strength of the joint. Rather, the actual joint strength is higher than that depicted in FIG. 13.

By comparison, the burs of butt jointed tool steel and tungsten carbide failed at the joint at loads of less than about 12 lbf (about 53 Newtons), specifically between about 8 lbf (about 36 Newtons) and about 11 lbf (about 49 Newtons). Additionally, as depicted, the load at failure for the stainless steel butt joint configuration is generally less than the exemplary burs of the present invention with many of these burs exhibiting loads at failure of less than about 5 lbf (about 22 Newtons). The minimum specification for use of the bur was about 5 lbf. Thus, many of the stainless steel butt jointed burs do not meet the required 5 lbf minimum. Further, the strength of the stainless steel butt joint varies greatly with only the strongest "non-outlier" strengths approaching the minimum "non-outlier" strengths of the exemplary burs of the present invention described above.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those of ordinary skill in the art. The invention in its broader aspects is therefore not limited to the specific details and illustrative examples shown and described. Accordingly, departures may be made from such details without departing from the scope of the general inventive concept.

What is claimed is:

1. A bur for use with a machine having a rotatable chuck, the bur comprising:
    an elongated member having a longitudinal axis and including a head and a shank that are made of dissimilar materials, the material of the head having a lower coefficient of thermal expansion than the material of the shank, and
    a joint between the head and the shank,
        the shank including a gripping portion adapted to cooperate with the rotatable chuck of the machine and a recess formed in one end of, and extending into, the shank in the direction of the longitudinal axis,
        the head extending along the longitudinal axis, and having a working surface adapted to remove material and a projecting portion that cooperates with the recess, wherein the projecting portion has a cone-like shape and the recess has a cup-like shape that complements the cone-like shape of the projecting portion,
        wherein the joint is formed at an interface between the projecting portion and the recess whereby a portion of the head that includes the projecting portion is compressively stressed.

2. The bur of claim 1 wherein the shank has a neck portion between the gripping portion and the recess, the neck portion having a cross-sectional dimension that is equal to or less than a cross-sectional dimension of the joint.

3. The bur of claim 1 wherein the cone-like shape of the projecting portion is a cone defined by a first angle at a vertex thereof.

4. The bur of claim 3 wherein the first angle is between about 40 ° and about 80 °.

5. The bur of claim 3 wherein the first angle is between about 55 ° and about 65 °.

6. The bur of claim 3 wherein the cone is a truncated cone.

7. The bur of claim 3 wherein the cup-like shape of the recess is a cone defined by a second angle at a vertex thereof, the second angle being greater than, equal to, or less than the first angle.

8. The bur of claim 1 wherein the cone-like shape of the projecting portion has a concave or convex surface and the cup-like shape of the recess has a convex or concave surface, respectively.

9. The bur of claim 1 wherein the bur contains a void in a region of the interface between the shank and the head.

10. The bur of claim 1 wherein the working surface further comprises a plurality of cutting edges that are arranged to remove material.

11. The bur of claim 1 wherein the material of the shank comprises stainless steel.

12. The bur of claim 1 wherein the material of the head comprises a carbide.

13. The bur of claim 1 wherein the average coefficient of thermal expansion of the material of the head is at least about 30% less than the average coefficient of thermal expansion of the material of the shank.

14. The bur of claim 13 wherein the material of the shank is stainless steel and the material of the head comprises metal carbide.

15. A dental bur for use with a dental handpiece having a rotatable chuck, the bur comprising:
an elongated member having a longitudinal axis and including a head and a shank that are made of dissimilar materials, and
a weld joint between the head and the shank,
the shank including a gripping portion adapted to cooperate with the rotatable chuck of the dental handpiece and the shank having a recess in one end of, and extending into, the shank in the direction of the longitudinal axis and a neck portion positioned between the head and the gripping portion, the neck portion having a cross-sectional dimension that is equal to or less than a maximum cross-sectional dimension of the weld joint, and
the head extending along the longitudinal axis and having a working surface adapted to remove tooth material and a projecting portion that cooperates with the recess,
wherein the weld joint is formed at an interface between the projecting portion and the recess such that a portion of the head that includes the projecting portion is compressively stressed.

16. The dental bur of claim 15 wherein the head comprises metal carbide and the shank comprises stainless steel.

17. A bur for use with a machine having a rotatable chuck, the bur comprising:
an elongated member having a longitudinal axis and including a head and a shank that are made of dissimilar materials, the material of the head having a lower coefficient of thermal expansion than the material of the shank, and
a weld joint between the head and the shank,
the shank including a gripping portion adapted to cooperate with the rotatable chuck of the machine and a recess formed in one end of, and extending into, the shank in the direction of the longitudinal axis,
the head extending along the longitudinal axis, and having a working surface adapted to remove material and a projecting portion that cooperates with the recess,
wherein the weld joint is formed at an interface between the projecting portion and the recess whereby a portion of the head that includes the projecting portion is compressively stressed.

18. The bur of claim 17 wherein the elongated member further includes a neck portion that tapers to a cross-sectional dimension that is the smallest cross-sectional dimension of the bur between the gripping portion and the working surface.

19. The bur of claim 17 wherein the elongated member further includes a neck portion having a cross-sectional dimension that is less than a cross-sectional dimension of the weld joint.

* * * * *